(12) United States Patent
Klee et al.

(10) Patent No.: US 9,155,481 B2
(45) Date of Patent: Oct. 13, 2015

(54) APPARATUS FOR MONITORING A POSITION OF A TUBE'S DISTAL END WITH RESPECT TO A BLOOD VESSEL

(75) Inventors: Marieke Klee, Eindhoven (NL); Jacob Roger Haartsen, Eindhoven (NL); Judith Margreet Rensen, Eindhoven (NL)

(73) Assignee: Koninklijke Philips N.V., Eindhoven (NL)

( * ) Notice: Subject to any disclaimer, the term of this patent is extended or adjusted under 35 U.S.C. 154(b) by 699 days.

(21) Appl. No.: 13/321,207

(22) PCT Filed: May 26, 2010

(86) PCT No.: PCT/IB2010/052346
§ 371 (c)(1),
(2), (4) Date: Nov. 18, 2011

(87) PCT Pub. No.: WO2010/136984
PCT Pub. Date: Dec. 2, 2010

(65) Prior Publication Data
US 2012/0071783 A1    Mar. 22, 2012

(30) Foreign Application Priority Data

May 28, 2009   (EP) .................................... 09161326

(51) Int. Cl.
*A61B 5/028*  (2006.01)
*A61B 5/02*   (2006.01)
(Continued)

(52) U.S. Cl.
CPC ............ *A61B 5/028* (2013.01); *A61B 5/02007* (2013.01); *A61B 5/06* (2013.01); *A61B 5/6848* (2013.01); *A61B 2560/0219* (2013.01); *A61B 2562/0271* (2013.01); *A61B 2562/043* (2013.01)

(58) Field of Classification Search
CPC ........ A61B 5/02; A61B 5/021; A61B 5/0215; A61B 5/02158; A61B 5/0285; A61B 5/028; A61B 5/06
USPC .......................... 600/504, 505, 549, 576–579
See application file for complete search history.

(56) References Cited

U.S. PATENT DOCUMENTS 3,595,079 A     7/1971  Grahn
4,319,483 A *   3/1982  Durham et al. ............ 73/204.15
(Continued)

FOREIGN PATENT DOCUMENTS

EP      1477113 A1   11/2004
JP    2000046678 A    2/2000
(Continued)

OTHER PUBLICATIONS

Tanse et al.; "Multi-Parameter Sensor System With Intravascular Navigation for Catheter/ Guide Wire Application" Sensors and Actuators A Physical; vol. 97-98, Apr. 1, 2002, ISSN: 0924-4247, XP004361591; pp. 116-124.

*Primary Examiner* — Max Hindenburg

(57) ABSTRACT

An apparatus for monitoring whether or not a distal end of a tube is positioned inside a blood vessel includes a heating element configured to heat the tube distal end, and a sensor arrangement configured to generate a measurement signal indicative for heat transferred by exterior of the distal end. The apparatus further includes a comparator configured to compare the measurement signal with a reference level. The reference level equals a value attained by the measurement signal in response to a minimum flow velocity in the blood vessel. Further, a system is configured to exchange a liquid with a mammal via a blood vessel. The system includes the apparatus having the tube.

19 Claims, 6 Drawing Sheets

(51) Int. Cl.
*A61B 5/06* (2006.01)
*A61B 5/00* (2006.01)

(56) References Cited

U.S. PATENT DOCUMENTS

| | | | |
|---|---|---|---|
| 4,971,068 A | 11/1990 | Sahi | |
| 5,311,871 A * | 5/1994 | Yock | 600/461 |
| 5,509,424 A | 4/1996 | Al-Ali | |
| 8,034,050 B2 | 10/2011 | Shiva | |
| 2003/0088245 A1* | 5/2003 | Woloszko et al. | 606/41 |
| 2004/0171977 A1 | 9/2004 | Paolini et al. | |
| 2004/0215067 A1* | 10/2004 | Stiger et al. | 600/300 |
| 2007/0016072 A1* | 1/2007 | Grunwald et al. | 600/468 |
| 2007/0078352 A1 | 4/2007 | Pijls | |
| 2008/0194977 A1 | 8/2008 | Bhunia | |

FOREIGN PATENT DOCUMENTS

| | | |
|---|---|---|
| JP | 2007222291 A | 9/2007 |
| JP | 2007260113 A | 10/2007 |
| JP | 2008520281 A | 6/2008 |
| WO | 2008069062 A1 | 6/2008 |
| WO | 2010004484 A1 | 1/2010 |

* cited by examiner

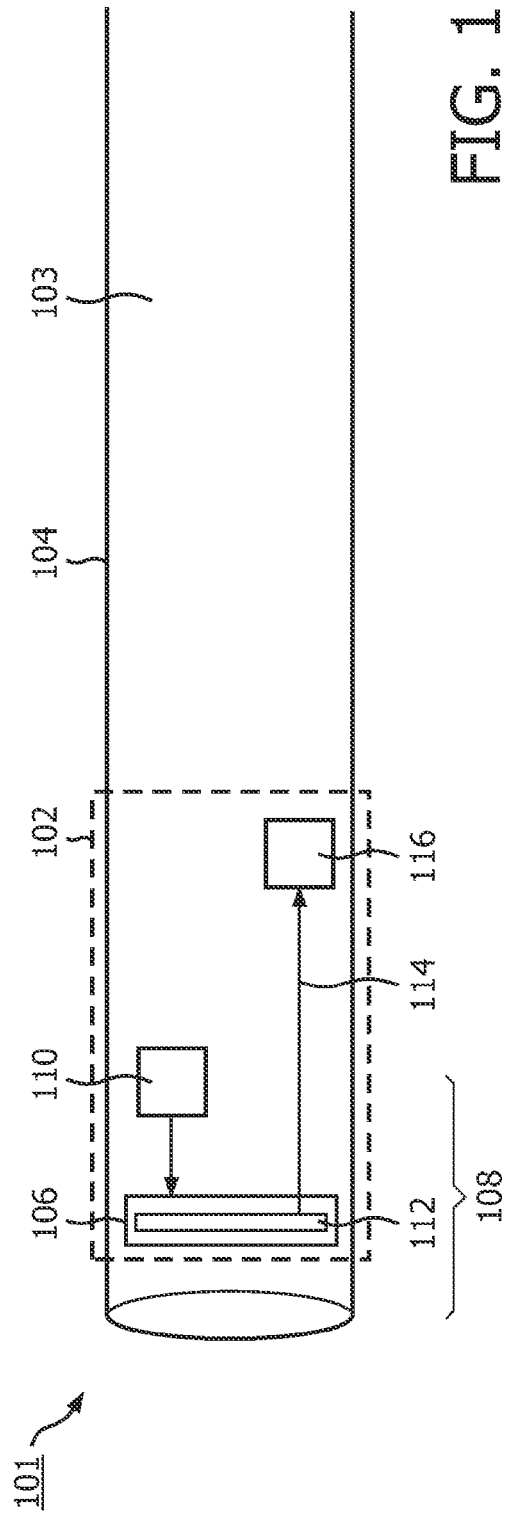
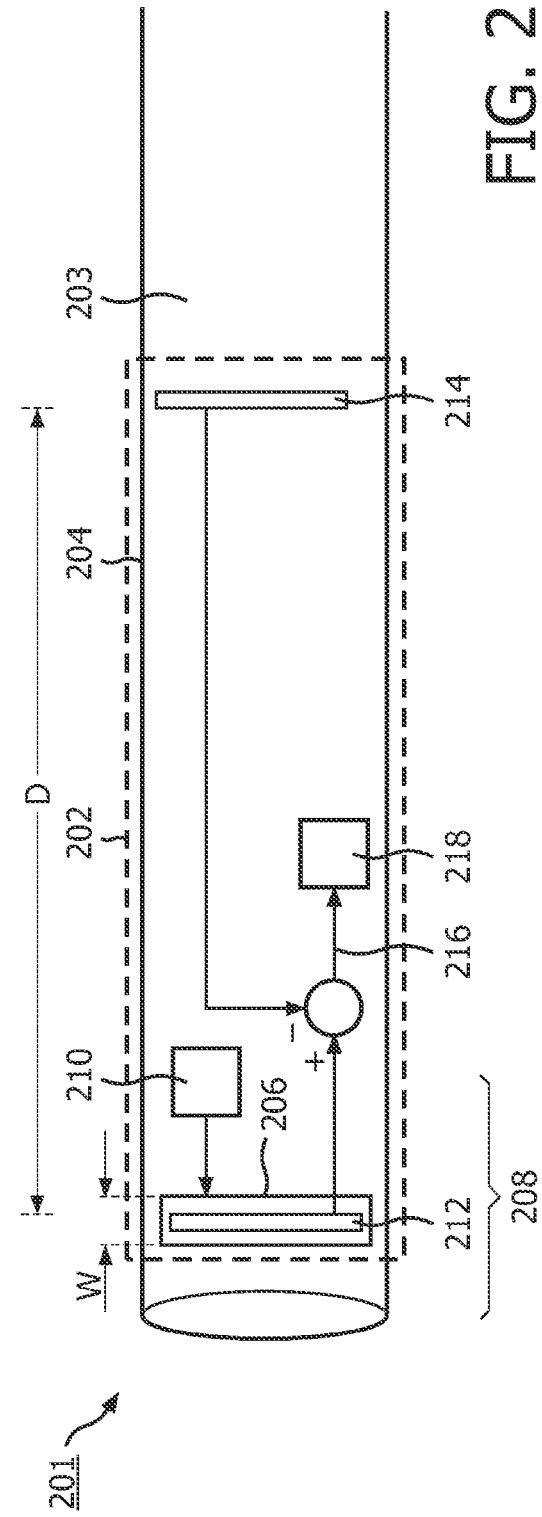

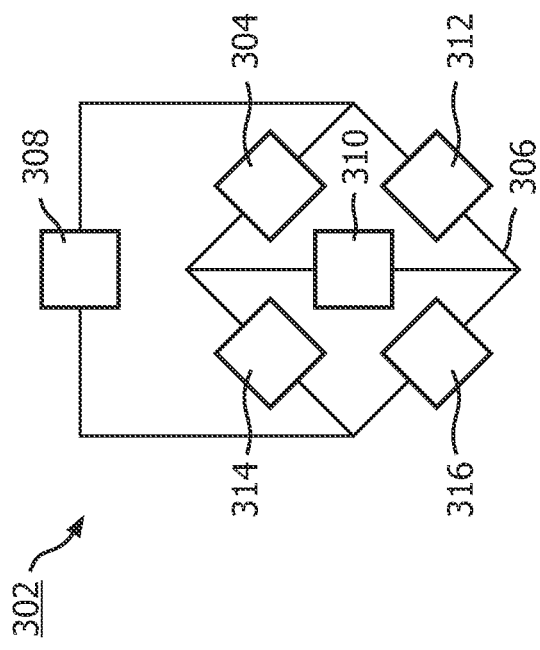
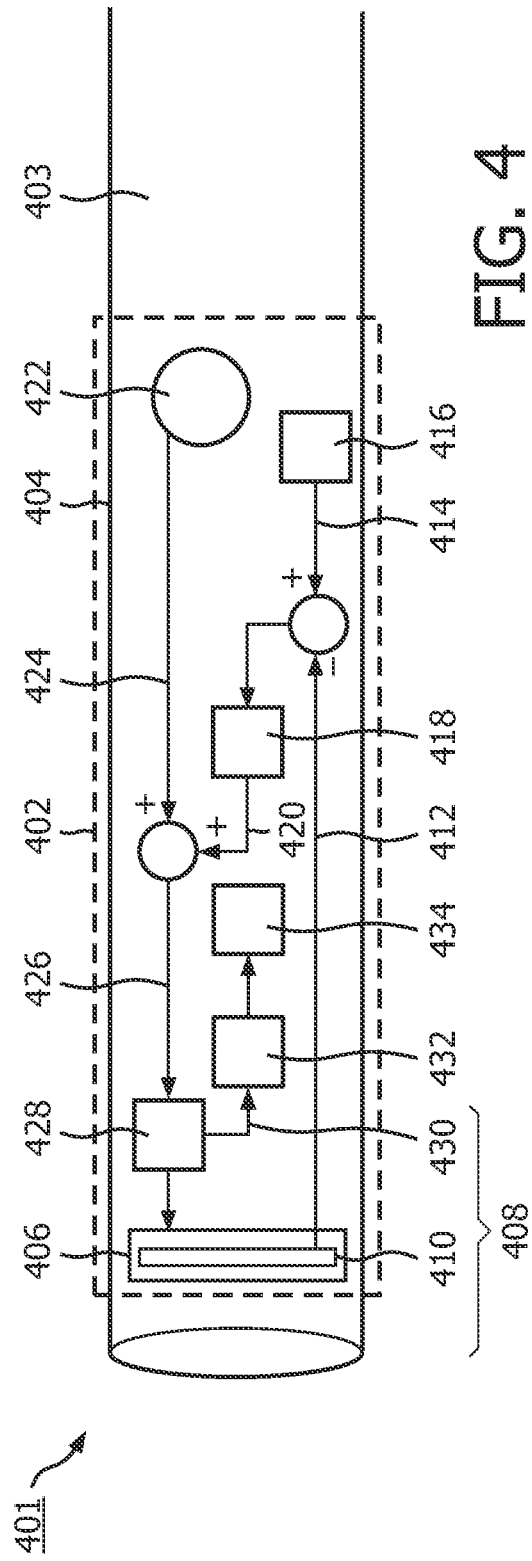

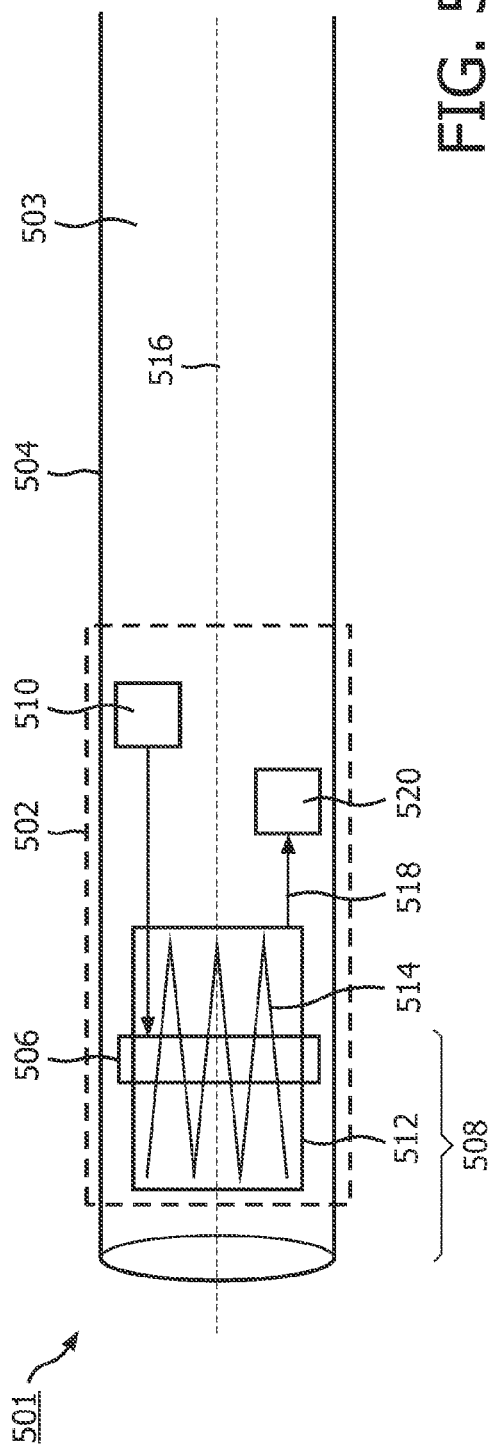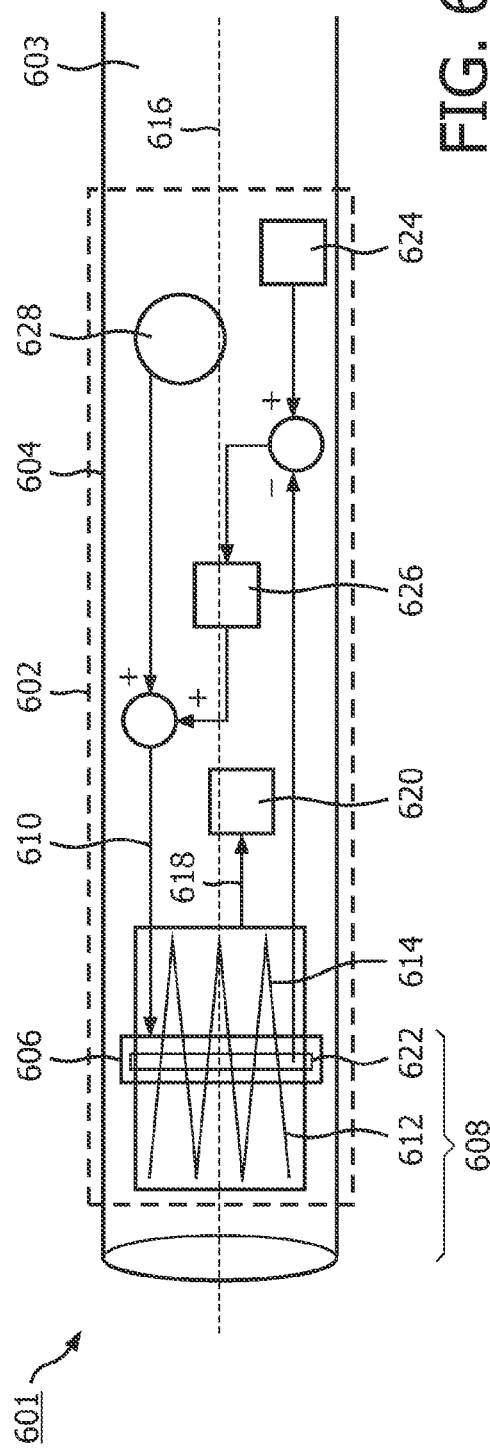

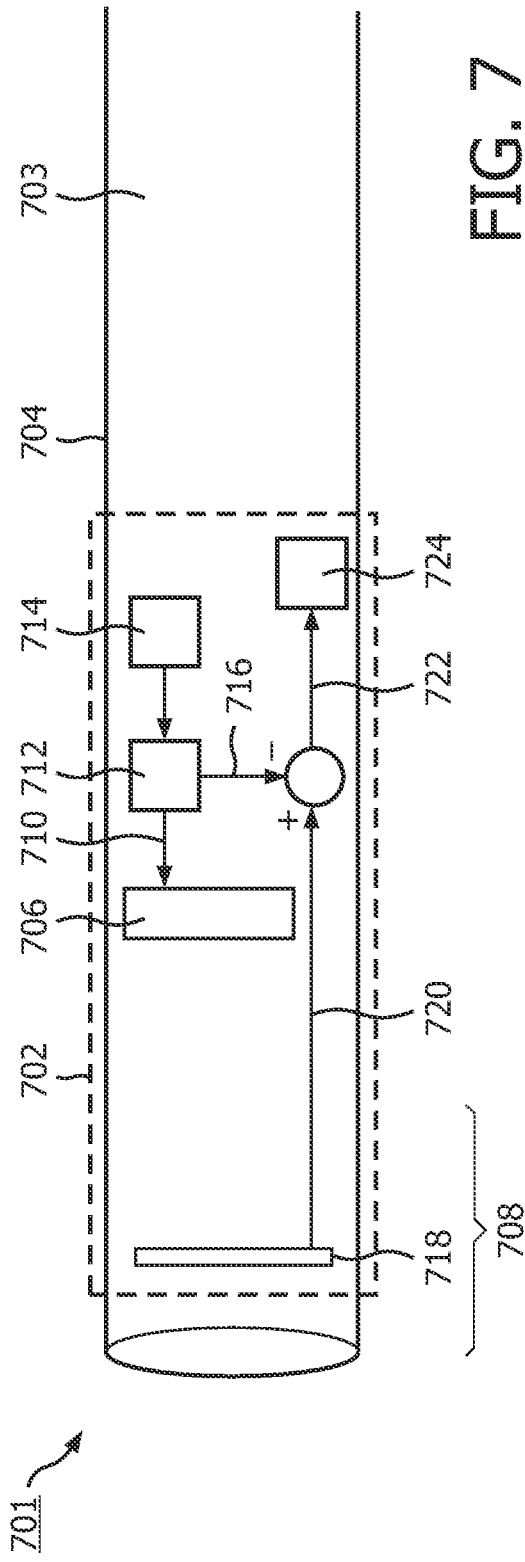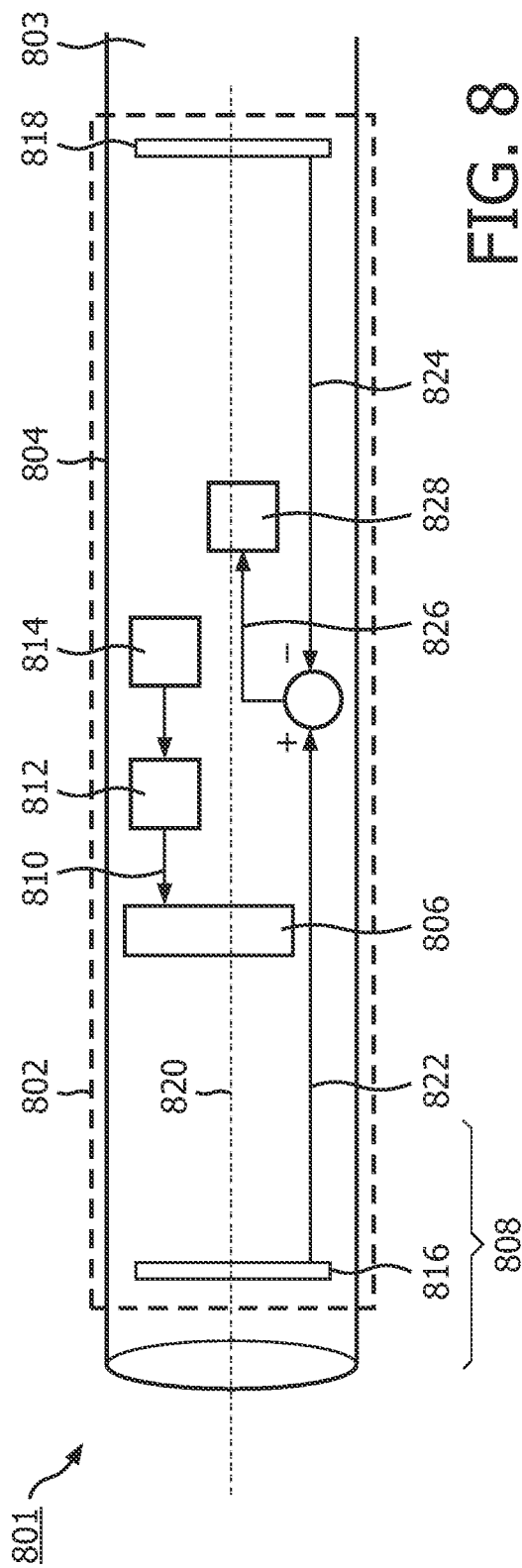

APPARATUS FOR MONITORING A POSITION OF A TUBE'S DISTAL END WITH RESPECT TO A BLOOD VESSEL

FIELD OF THE INVENTION

The invention relates to an apparatus for monitoring a position of a distal end of a tube with respect to a blood vessel.

The invention further relates to a system for exchanging a liquid via a blood vessel.

BACKGROUND OF THE INVENTION

U.S. Pat. No. 4,971,068 discloses a needle comprising a metal cannula and a temperature sensitive indicator mounted on the cannula. Blood vessel penetration is visually indicated by a change of color of the temperature sensitive indicator in case blood enters the cannula and reaches said temperature sensitive indicator.

A problem of the needle disclosed in U.S. Pat. No. 4,971,068 is that it is not capable of monitoring whether or not the cannula maintains a positioning inside the blood vessel during infusion procedures, i.e. procedures in which a liquid is supplied to the patient. Namely, the needle disclosed in U.S. Pat. No. 4,971,068 requires blood itself to flow into the cannula up to the temperature sensitive indicator in order to observe blood vessel penetration hence to observe the positioning of the cannula in the blood vessel.

SUMMARY OF THE INVENTION

It is an object of the invention to provide an apparatus of the kind defined in the opening paragraph, capable of monitoring whether or not a positioning inside a blood vessel is maintained for a distal end of a tube.

The object of the invention is achieved by the apparatus according to the invention. The apparatus according to the invention comprises a heating element configured for heating the distal end, a sensor arrangement for generating a measurement signal indicative for heat transferred by the exterior of the distal end, and a comparator arrangement for comparing the measurement signal with a reference level, wherein the reference level equals a value attained by the measurement signal in response to a minimum flow velocity in the blood vessel.

Given a level of power provided to the heating element, depending on the flow velocity of the blood in the blood vessel, heat transfer from the exterior of the distal end will significantly differ for positions in- and outside of the blood vessel. By generating a measurement signal indicative for heat transfer by the exterior of the tube's distal end, a position of the tube's distal end inside the blood vessel is made discernible from a position outside of the blood vessel. Herein the reference level equals the value attained by the measurement signal in response to the minimum flow velocity in the blood vessel, which value corresponds to a minimum level of heat transfer. Hence, in case the measurement signal indicates a higher level of heat transfer compared with the reference level, the tube's distal end must be positioned inside the blood vessel. Consequently, in case the measurement signal indicates a smaller level of heat transfer in comparison with the reference level, the tube's distal end must be positioned outside the blood vessel. So, through comparing the measurement signal with the reference level, it is ascertainable whether or not the distal end indeed occupies a position inside the blood vessel.

Based on the latter comparison the medical professional is informed regarding the positioning of the distal end. That is, the comparator arrangement furthermore generates a signal indicative for the positioning of the distal end with respect to the blood vessel based on comparing the measurement signal with the reference level.

It is to be noted that for monitoring the position of the distal end, blood flow outside the tube is employed. Hence, no blood is required to permanently flow through the tube. As a result, the apparatus according to the invention is capable of monitoring the position of the distal end relative to the blood vessel during sample taking procedures in which blood is drawn from a patient via the tube, as well as infusion procedures in which a liquid will flow through the tube towards the blood vessel.

Both during sample taking procedures and infusion procedures, the position of the distal end inside is prone to disturbances due to e.g. a patient's movements. In case the distal end position inside the blood vessel perishes, i.e. the distal end is no longer inside the blood vessel, the liquid is supplied to a tissue surrounding said blood vessel. As a result of that, irritation, swelling and/or pain are caused for the patient.

It is furthermore to be noted that the apparatus according to the invention is suitable for monitoring the tube's distal end positioning during all stages of such procedures, that is, not only during a process of exchanging a fluid with the patient but also at a beginning of such a procedure which beginning is dedicated to blood vessel penetration.

In this document, a blood vessel is considered to include both veins and arteries.

In a preferred embodiment of the apparatus according to the invention, the sensor arrangement comprises a first temperature sensor for measuring a temperature of the heating element while the heating element is provided with a constant level of power. This embodiment has the advantage of comprising a relatively small amount of electronic components, thereby allowing for miniaturization of the apparatus according to the invention and for a reduction of costs in manufacturing said apparatus. The latter quality enhances the disposability for the apparatus according to the invention. That is, this embodiment makes the financial loss caused by disposing the apparatus to be substantially small. Obviously, the apparatus according to the invention does not necessarily need to be disposed of, i.e. it does allow for a prolonged use.

In a further preferred embodiment of the apparatus according to the invention, the sensor arrangement comprises a secondary temperature sensor configured for measuring a temperature at a location substantially remote from the heating element, wherein the sensor arrangement is configured for measuring a difference between temperatures measured by the primary and secondary temperature sensors. Herein, a location substantially remote from the heating element implies a location having a temperature that is barely affected by heat transfer due to the heating element. This embodiment is advantageous in that it is capable of accurately registering the positioning of the tube's distal end since it is robust regarding ambient temperature fluctuations. Namely, said fluctuations are compensated for by grounding the measurement signal on the difference between temperatures measured by the first and second temperature sensors.

A further preferred embodiment of the apparatus according to the invention comprises a control circuit for controlling the power provided to the heating element on the basis of a deviation between a constant reference temperature and the temperature of the heating element measured by a primary temperature sensor, wherein the sensor arrangement is configured for measuring the power provided to the heating element. This embodiment has the advantage that an excessive heating of the blood inside the blood vessel and the tissue surrounding the blood vessel, is prevented from by controlling the temperature of the heating element at a constant reference temperature.

In a further preferred embodiment of the apparatus according to the invention, the sensor arrangement comprises a primary temperature sensor configured for measuring a difference between temperatures at predetermined locations on both sides of the heating element along an axis having a component parallel to a longitudinal axis of the tube while the heating element is provided with a constant level of power during operation. This embodiment is advantageous in that it is capable of measuring a flow direction in the blood vessel. This quality is of particular benefit in applications wherein it is essential to position the distal end in either an artery or a vein, which blood vessels carry blood along different flow directions. Hence, this embodiment effectively enables distinguishing between an artery and a vein.

In a further preferred embodiment of the apparatus according to the invention, the sensor arrangement comprises a primary temperature sensor configured for measuring a difference between temperatures at predetermined locations on both sides of the heating element along an axis having a component parallel to a longitudinal axis of the tube, wherein the power provided to the heating element during operation is controlled by a control circuit on the basis of a deviation between a constant reference temperature and the temperature of the heating element measured by a secondary temperature sensor. This embodiment is advantageous in that it increases a sensitivity of monitoring whether or not the distal end is located inside the blood vessel. Namely, in case the tube's distal end is positioned outside the blood vessel, a value of the measurement signal generated by this embodiment will significantly differ from the reference level. In addition to that, this embodiment is advantageous in that it prevents excessive heating from the blood inside the blood vessel and the tissue surrounding the blood vessel. Furthermore, this embodiment is advantageously capable of measuring the direction of blood flow in the blood vessel.

In a further practical embodiment of the apparatus according to the invention, the sensor arrangement comprises a primary temperature sensor for measuring a temperature of the exterior of the tube's distal end while the heating element is provided with power pulses during operation, wherein the sensor arrangement is configured for measuring a duration after which the heat pulses are detected by the primary temperature sensor.

In a further preferred embodiment of the apparatus according to the invention, the sensor arrangement comprises a primary temperature sensor and a secondary temperature sensor, wherein the primary and secondary temperature sensors are situated at locations on both sides of the heating element along an axis having a component parallel to a longitudinal axis of the tube, wherein the heating element is provided with power pulses during operation, and wherein the sensor arrangement is configured for measuring a difference between durations after which the heat pulses are detected by the primary and secondary temperature sensors. This embodiment is advantageous in that it is capable of measuring the direction of blood flow in the blood vessel. This quality is of particular benefit in applications wherein it is essential to position the tube's distal end in either an artery or a vein, which blood vessels carry blood along different flow directions. Hence, this embodiment effectively enables distinguishing between an artery and a vein.

A further preferred embodiment of the apparatus according to the invention comprises an antenna for RF communication and a coil for receiving electromagnetic radiation for powering the heating element. This embodiment has the advantage that the sensor arrangement and the heating element allow for wireless operation, that is, the sensor arrangement and the heating element are physically entirely disconnected from any circuitry that drives the heating element and responds to the measurement signal generated by the sensor arrangement. As a result, no bothersome wiring is to be attached to the tube. The absence of such wiring largely facilitates the medical professional in handling the apparatus according to the invention.

In a preferred embodiment of the apparatus according to the invention, the heating element and the sensor arrangement are processed on a silicon substrate attached to a mechanically flexible carrier. This embodiment advantageously enables the sensor arrangement and the heating element to be conformable to a geometry of the tube, e.g. a tube having a circular or a rectangular cross-section. As a result, depending on a particular application of the apparatus according to the invention, a wide range of geometries may be employed for the tube.

In a practical embodiment of the apparatus according to the invention, the sensor arrangement comprises a temperature sensor comprising a doped polysilicon thermopile.

It is a further object of the invention to provide a system of the kind defined in the opening paragraph. This object is achieved by the system according to the invention. The system according to the invention comprises a tube, wherein the tube is provided with the apparatus according to the invention.

In a preferred embodiment of the system according to the invention, the heating element and the sensor arrangement are arranged substantially co-axially with the tube. In this text, co-axially is to be interpreted as an arrangement of bodies or surfaces sharing a common axis in longitudinal direction. Hence, both circular and non-circular bodies and surfaces allow for a co-axial arrangement. This embodiment advantageously increases the accuracy with which the positioning of the tube's distal end is detectable. Namely, by co-axially arranging the sensor arrangement, the heating element and the tube, plane symmetry is created in a plane extending through a cross-section of the tube. The latter plane symmetry allows for spatially more evenly heating the exterior of a tube's distal end, and for spatially more refined generating the measurement signal indicative for the heat transferred by the exterior of the tube's distal end to its environment.

In a further preferred embodiment of the system according to the invention, the heating element and the sensor arrangement are situated in a wall of the tube. This embodiment has the advantage that it prevents the sensor arrangement and the heating element from physically contacting the blood in the blood vessel as well as the fluid to be exchanged via the tube. The latter quality is essential for medical applications such as intravenous infusion. Namely, in these applications it is utterly important to prevent an emergency situation in which the sensor arrangement, the heating element and/or their parts are released. Preferably, both the sensor arrangement and the heating element are installed in a relatively close proximity of an outer surface of the tube in order to reduce a thermal resistance due to a distance between the blood and the sensor arrangement and the heating element.

BRIEF DESCRIPTION OF THE DRAWINGS

FIG. 1 schematically displays an embodiment of the system according to the invention, wherein the apparatus according to the invention comprises a primary temperature sensor for measuring a temperature of the heating element.

FIG. 2 schematically shows an embodiment of the system according to the invention, wherein the apparatus according to the invention comprises a secondary temperature sensor for compensating ambient temperature fluctuations.

FIG. 3 schematically depicts an embodiment of an electronic circuit for materializing the sensor arrangement and the heating element according to the embodiment depicted in FIG. 2.

FIG. 4 schematically displays an embodiment of the system according to the invention, wherein the apparatus according to the invention comprises a control circuit for controlling the heating element's temperature.

FIG. 5 schematically shows an embodiment of the system according to the invention, wherein the apparatus according to the invention comprises primary and secondary temperature sensors situated on both sides of the heating element.

FIG. 6 schematically displays an embodiment of the system according to the invention, wherein the apparatus according to the invention comprises primary and secondary temperature sensors situated on both sides of the heating element and a feedback controller for maintaining a reference temperature for the heating element.

FIG. 7 schematically depicts an embodiment of the system according to the invention, wherein the apparatus according to the invention comprises a heating element that is provided with a series of power pulses.

FIG. 8 schematically shows an embodiment of the system according to the invention, wherein the apparatus according to the invention comprises primary and secondary temperature sensors situated on both sides of the heating element, wherein the heating element is provided with power pulses.

DETAILED DESCRIPTION OF THE EMBODIMENTS

Figure 9:
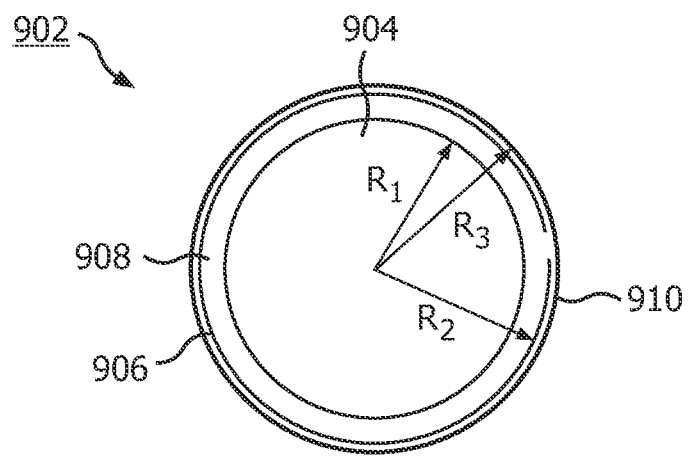
FIG. 9 schematically displays an embodiment of the system according to the invention wherein the sensor arrangement and the heating element are situated in a wall of a tube.

FIG. 1 schematically shows a system 101 for exchanging a liquid 103 with a mammal via a blood vessel. The system comprises a tube 104, and an apparatus 102 for monitoring a position of a distal end 108 of the tube 104 with respect to the blood vessel. A heating element 106 is embedded in the tube 104 for heating an exterior of the distal end 108 during operation. For this purpose the heating element 106 is provided with a constant power by an energy source 110, for instance a battery. A temperature sensor 112 known per se, is configured for measuring a temperature of the heating element 106. A measurement signal 114 relates to the temperature of the heating element 106. Assuming a constant tissue temperature, the measurement signal 114 is indicative for a heat transferred by the exterior of the distal end 108 to its environment, i.e. blood surrounding the distal end 108 in case it is positioned inside the blood vessel or tissue surrounding the blood vessel in case the distal end 108 in case is positioned outside the blood vessel. A comparator arrangement 116 is configured for comparing the measurement signal 114 with a reference level. In this particular example, the reference level equals the temperature attained by the heating element 106 in response to a minimum flow velocity in the blood vessel. If the distal end 108 is positioned in the blood vessel, depending on the flow velocity of the blood, the temperature of the heating element 106 will significantly decrease compared to the temperature that the heating element 106 will obtain if the tube's distal end 108 is positioned outside of the blood vessel. Hence, the reference level corresponds to a maximum value for the temperature of the heating element 106 given the power provided to it during operation.

FIG. 2 schematically shows a system 201 for exchanging a liquid 203 with a mammal via a blood vessel. The system comprises a tube 204, and an apparatus 202 for monitoring a position of a distal end 208 of the tube 204 with regard to the blood vessel. A heating element 206 is embedded in the tube 204 for heating an exterior of the tube's distal end 208 during operation. For this purpose the heating element 206 is provided with a constant power by an energy source 210. A primary temperature sensor 212, e.g. a thermometer, is configured for measuring a temperature of the heating element 206. A secondary temperature sensor 214 is remotely located from the heating element 106 at a distance D. Herein the distance D preferably exceeds a width W of the heating element 206 by at least a factor 5 in order to minimize the influence of the heating element 206 on the temperature of the secondary temperature sensor 214. The secondary temperature sensor 214 is configured for measuring an ambient temperature. A measurement signal 216 relates to a difference between temperatures measured by the primary temperature sensor 212 and the secondary temperature sensor 214. A comparator arrangement 218 is configured for comparing the measurement signal 216 with a reference level. In this particular example, the reference level equals the difference between the temperature of the heating element 206 and the ambient temperature in response to a minimum flow velocity of blood. In case the distal end 208 is positioned in the blood vessel, depending on the flow velocity of the blood, the temperature of the heating element 206 significantly reduces compared to the temperature it will obtain in case the tube's distal end 208 is positioned outside of the blood vessel. Therefore the reference level corresponds to a maximum value for the temperature of the heating element 206 hence a maximum value for the difference between the temperature of the heating element 206 and the ambient temperature.

FIG. 3 schematically depicts an electronic circuit 302 for realizing a sensor arrangement and a heating element. The electronic circuit 302 comprises a thermistor 304 having a predetermined relation between its electrical resistance and its temperature performs as a heating element. Referring to e.g. FIG. 2, the thermistor is configured for heating the tube's distal end 208. Referring to FIG. 3, the thermistor 304 is embedded in a Wheatstone bridge 306. A controlled voltage source 308 applies a voltage across the Wheatstone bridge 306. A Voltmeter 310 is configured for indirectly measuring the temperature of the thermistor 304 through employing the predetermined relation between the thermistors resistance and its temperature, thereby performing as a resistance thermometer. Fluctuations in ambient temperature are accounted for by situating a reference thermistor 312 remotely from the thermistor 304. For that purpose, the reference thermistor 312 is provided with a relatively large electrical resistance to guarantee minimum dissipation. In addition, the thermistor 304 and the reference thermistor 312 are provided with substantially equal temperature coefficients. Furthermore, resistors 314 and 316 are comprised in the Wheatstone bridge 306. The resistors 314 and 316 are preferably provided with negligible temperature coefficients compared to the thermistor 304.

FIG. 4 schematically shows a system 401 for exchanging a liquid 403 with a mammal via a blood vessel. The system comprises a tube 404, and an apparatus 402 for monitoring a position of a distal end 408 of the tube 404 with regard to the blood vessel. A heating element 406 is embedded in the tube 404 for heating an exterior of the tube's distal end 408 during operation. A temperature sensor 410 is configured for measuring the temperature of the heating element 406. An output 412 of the temperature sensor 410 is compared to a constant reference temperature provided via an output 414 of a set-point generator 416. A deviation between the output 412, i.e. the temperature of the heating element 406, and the output 414, i.e. the constant reference temperature, is fed into a controller 418. In this particular example, the controller 418 is a Proportional Integral Derivative (PID) controller. The controller 418 translates said deviation into a power 420. A coil 422 is provided in the system 402 for providing a further power 424 upon receiving an electromagnetic radiation during operation, for instance by inductive coupling. A sensor 428 is configured for measuring a total power 426 supplied to the heating element 406, i.e. a power required for maintaining a constant reference temperature for the heating element 406 given the fact that blood flow will cool the heating element 406, and for generating a measurement signal 430. A comparator arrangement 432 is arranged for comparing the measurement signal 430 with a reference level. In this specific example, the reference level amounts to a value required for the total power 426 to keep the heating element 406 at the constant reference temperature in response to minimum flow conditions. That is, if the tube's distal end 408 is positioned in the mammal's blood vessel, the amount of heat transferred by the exterior of the tube's distal end 408 to its environment significantly increase with increasing blood flow velocity. Therefore, the total power 426 required to maintain the constant reference temperature for the heating element 406 significantly increases with increasing blood flow velocity. Alternatively, if the further power 424 is predetermined, measuring the power 422 would be feasible as well for monitoring whether or not the tube's distal end is located inside the blood vessel.

FIG. 5 schematically shows a system 501 for exchanging a liquid 503 with a mammal via a blood vessel. The system comprises a tube 504, and an apparatus 502 for monitoring a position of a distal end 508 of the tube 504 with regard to the blood vessel. A heating element 506 is embedded in the tube 504 for heating an exterior of the tube's distal end 508 during operation. For that purpose, a power source 510 provides the heating element 506 with a constant level of power during operation. A temperature sensor 512 is configured for measuring a difference between temperatures at locations on both sides of the heating element 506. For that purpose the temperature sensor 512 comprises a thermopile 514. In this document, a thermopile refers to series connection of thermocouples. A thermopile generates an output relating to a local temperature gradient or to a local temperature difference rather than to an absolute temperature. Hence, the thermopile 514 registers a difference between temperatures at locations on both sides of the heating element 506. Herein, the locations are situated along an axis having a component parallel to a longitudinal axis 516 of the tube. The temperature sensor generates a measurement signal 518. The larger the blood flow velocity, the larger the temperature asymmetry across the heating element 506 will become. That is, heat will be transferred via forced convection of the blood flow from the heating element 506 to one side of the thermopile. A comparator element 520 is arranged for comparing the measurement signal 518 with a reference level. In this example, the reference level equals the value that would be attained by the temperature difference across the heating element 506 in response to a minimum flow velocity of the blood in the blood vessel and to the power provided to the heating element during operation. Namely, for minimum flow velocity, the asymmetry of temperatures across the heating element 506 will be minimal. Increasing blood flow velocity causes said asymmetry to enlarge which results in an increase of an absolute value of the measurement signal 518. A sign of the measurement signal 518 is indicative for the flow direction of the blood in the blood vessel. The comparator arrangement 520 may be additionally configured for comparing the sign of the measurement signal 518 with a further reference value, which further reference value is indicative for either one of the possible flow directions.

FIG. 6 schematically shows a system 601 for exchanging a liquid 603 with a mammal via a blood vessel. The system comprises a tube 604, and an apparatus 602 for monitoring a position of a distal end 608 of the tube 604 with regard to the blood vessel. A heating element 606 is embedded in the tube 604 for heating an exterior of the tube's distal end 608 during operational conditions. For that purpose, a power 610 is provided to the heating element 606. A primary temperature sensor 612 is configured for measuring temperatures at locations on both sides of the heating element 606. For that purpose the primary temperature sensor 612 comprises a thermopile 614. Herein, the locations are situated along an axis having a component parallel to a longitudinal axis 616 of the tube 604. The primary temperature sensor 612 generates a measurement signal 618. A comparator element 620 is arranged for comparing the measurement signal 618 with a reference level. In this example, the reference level equals the value attainable by the difference in temperatures at the locations on both sides of the heating element 606, in response to a minimum flow velocity of blood in the blood vessel, and to the power provided to the heating element during operation. Namely, increasing blood flow velocity causes said difference in temperature to increase. That is, if the tube's distal end is in the blood vessel, heat will be transferred from the exterior of the tube's distal end 608 along with the blood flow. Said heat transfer brings into being a temperature asymmetry with regard to the locations on both sides of the heating element 606 and therefore causes an absolute value of the measurement signal 618 to increase. A sign of the measurement signal 618 is indicative for the flow direction of the blood in the blood vessel. The comparator arrangement 620 may be additionally configured for comparing the sign of the measurement signal 618 with a further reference value, which further reference value is indicative for either one of the possible flow directions. A secondary temperature sensor 622 known per se is configured for measuring the temperature of the heating element 606. The temperature of the heating element 606 is compared with a constant reference temperature provided by a set point generator 624. A deviation between said temperatures is fed into a controller 626, which is a Proportional (P) controller in this specific example. An output of the controller 626 added with a further power provided by a coil 628, which coil is arranged for generating the further power upon receiving an electromagnetic radiation, constitutes the power 610 provided to the heating element 606 during operational conditions. Preferably, the thermopile 614 and the heating element 606 are situated symmetrically with regard to the longitudinal axis 616 of the tube 604.

FIG. 7 schematically shows a system 701 for exchanging a liquid 703 with a mammal via a blood vessel. The system comprises a tube 704, and an apparatus 702 for monitoring a position of a distal end 708 of the tube 704 with regard to the blood vessel. A heating element 706 is embedded in the tube 704 for heating an exterior of the tube's distal end 708 during operation. For that purpose, the heating element 706 is provided with a series of power pulses 710 by a pulse generator 712. Preferably, the series of power pulses 710 is realized a square wave of power pulses. Herein, a series of power pulses comprises at least two pulses, but preferably significantly more than two pulses in order to enable permanently monitoring a position of the tube's distal end 708. The pulse generator 712 is supplied with power by the power source 714. The pulse generator 712 generates a signal 716 indicative for points of time at which rising flanks in the series of power pulses 710 are generated. A temperature sensor 718 is arranged for measuring a temperature at an exterior of a tube's distal end 708. The temperature sensor 718 is additionally configured for generating an output 720 indicative further points of time at which rising flanks of temperature pulses are registered by the temperature sensor 718. A measurement signal 722 relates to a difference between the points of time and the further points of time. A comparator element 724 known per se compares the measurement signal 722 with a reference level. Herein the reference level amounts to a value for time span between a generation of a rising flank of a power pulse by the pulse generator 712 and a detection of a corresponding temperature pulse by the temperature sensor 718, which value is attained in response to a minimum flow velocity of the blood in the blood vessel and to the power provided to the heating element 706. The latter time span will attain a maximum value in response to a minimum flow velocity and will decrease with increasing flow velocity.

FIG. 8 schematically shows a system 801 for exchanging a liquid 803 with a mammal via a blood vessel. The system comprises a tube 804, and an apparatus 802 for monitoring a position of a distal end 808 of the tube 804 with regard to the blood vessel. A heating element 806 is embedded in the tube 804 for heating an exterior of the tube's distal end 808 during operation. For that purpose, the heating element 806 is provided with a series of power pulses 810 by a pulse generator 812. The pulse generator 812 is supplied with power by the power source 814 during operation. The system 802 comprises a primary temperatures sensor 816 and a secondary temperature sensor 818. Herein, the primary temperature sensor 816 and the secondary temperature sensor 818 are situated at locations on both sides of the heating element 806 along an axis having a component parallel to a longitudinal axis 820 of the tube 804. Preferably, the primary and secondary temperature sensors 816 and 818 are situated symmetrically with regard to the heating element 806 along the axis parallel to the longitudinal axis 820. Namely, no differences in the positions of the first and secondary temperature sensors 816 and 818 relative to the heating element 806 have to be accounted for. The primary temperature sensor 816 is arranged for measuring a temperature at an exterior of a tube's distal end 808. The temperature sensor 816 is additionally configured for generating an output 822 indicative for points of time at which rising flanks of temperature pulses are registered by the primary temperature sensor 816. The secondary sensor 818 is configured for measuring a temperature at the exterior of the tube 804 on a position on an on an opposite site of the heating element 806. The secondary temperature sensor 818 is additionally configured for generating an output 824 indicative for further points of time at which rising flanks of further temperature pulses are registered by the secondary temperature sensor 818. Herein, the temperature pulses and the further temperature pulses are induced by the power pulses 814 during operation. A measurement signal 826 relates to a difference between the output 822 and the further output 824, i.e. a difference between the points of time and the further points of time at which the temperature pulses and the further temperature pulses are detected by the primary and secondary temperature sensors 816 and 818, respectively. A comparator element 828 known per se compares the measurement signal 826 with a reference level. Herein, the reference level amounts to a value of the time span between the point of time at which the rising flank is detected by the primary temperature sensor 816 and the further point of time at which the further rising flank is detected by the secondary temperature sensor 818, which time span is attained in response to a minimum flow velocity of the blood in the blood vessel and to the power provided to the heating element 806. The aforementioned time span will attain a minimum value in response to a minimum blood flow velocity, and will increase with increasing blood flow velocity.

Figure 10:
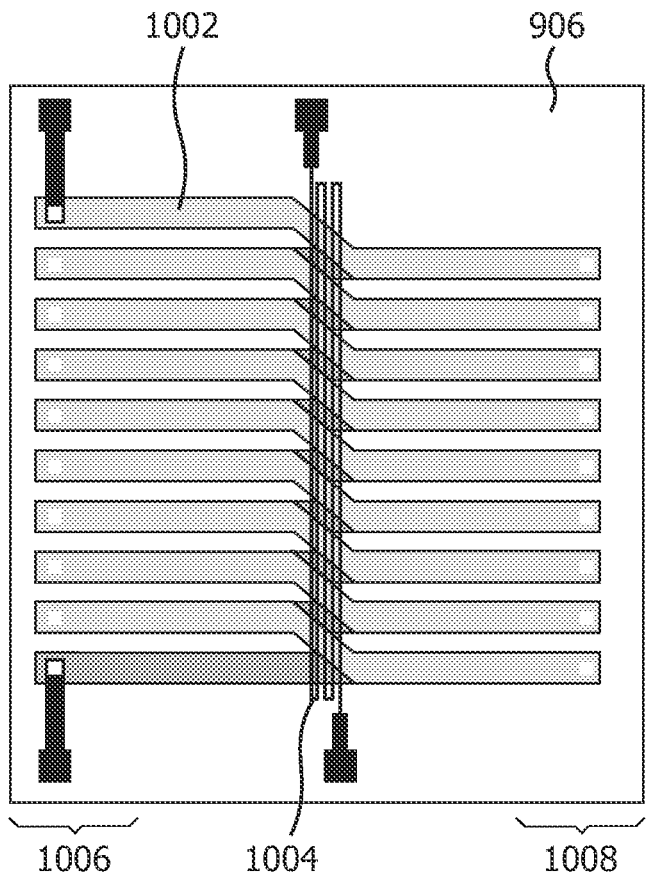
FIG. 10 schematically shows a plan view of the embodiment depicted in FIG. 9.

FIG. 9 schematically displays an embodiment of a system 902 for exchanging a fluid 904 with a mammal via a blood vessel. A sensor arrangement and a heating element are processed in a silicon substrate attached to a mechanically flexible carrier 906. Referring to FIG. 10, which figure schematically depicts a plan view of the carrier 906, the carrier 906 comprises a thermopile 1002. In this specific example, the thermopile 1002 is realized in thin film technology by a semiconductor material. Herein junctions of the thermopile 1002 are materialized via doping of the semiconductor material. Alternatively, the thermopile 1002 is manufactured from a metal, e.g. aluminum. A heating element is 1004 is realized by a metal wire, e.g. aluminum. The thermopile 1002 measures a difference between temperatures on both sides of the heating element 1004. More specifically, temperatures are measured at junctions 1006 and further junctions 1008. Referring to FIG. 9, the carrier 906 is situated in a wall 908 of a tube 910. The wall 908 is made of a suitable plastic such as poly-imide. The tube 910 has an inner radius R1 and an outer radius R3. The carrier 906 is arranged co-axially with the tube 910 at a radius R2 for which it holds that R1<R2<R3. Preferably, to reduce a thermal resistance between blood and the carrier 906, with the purpose of increasing an accuracy of monitoring the positioning of a tube's distal end, the distance R3-R2 is relatively small, e.g. at about 60 μm. Clearly, the carrier 906 does not physically contact the blood potentially surrounding the tube 910. Preferably, the carrier 906 and consequently the sensor arrangement and the heating element processed therein, constitute a relatively large arc in order to generate a spatially highly refined measurement signal.

Figure 11:
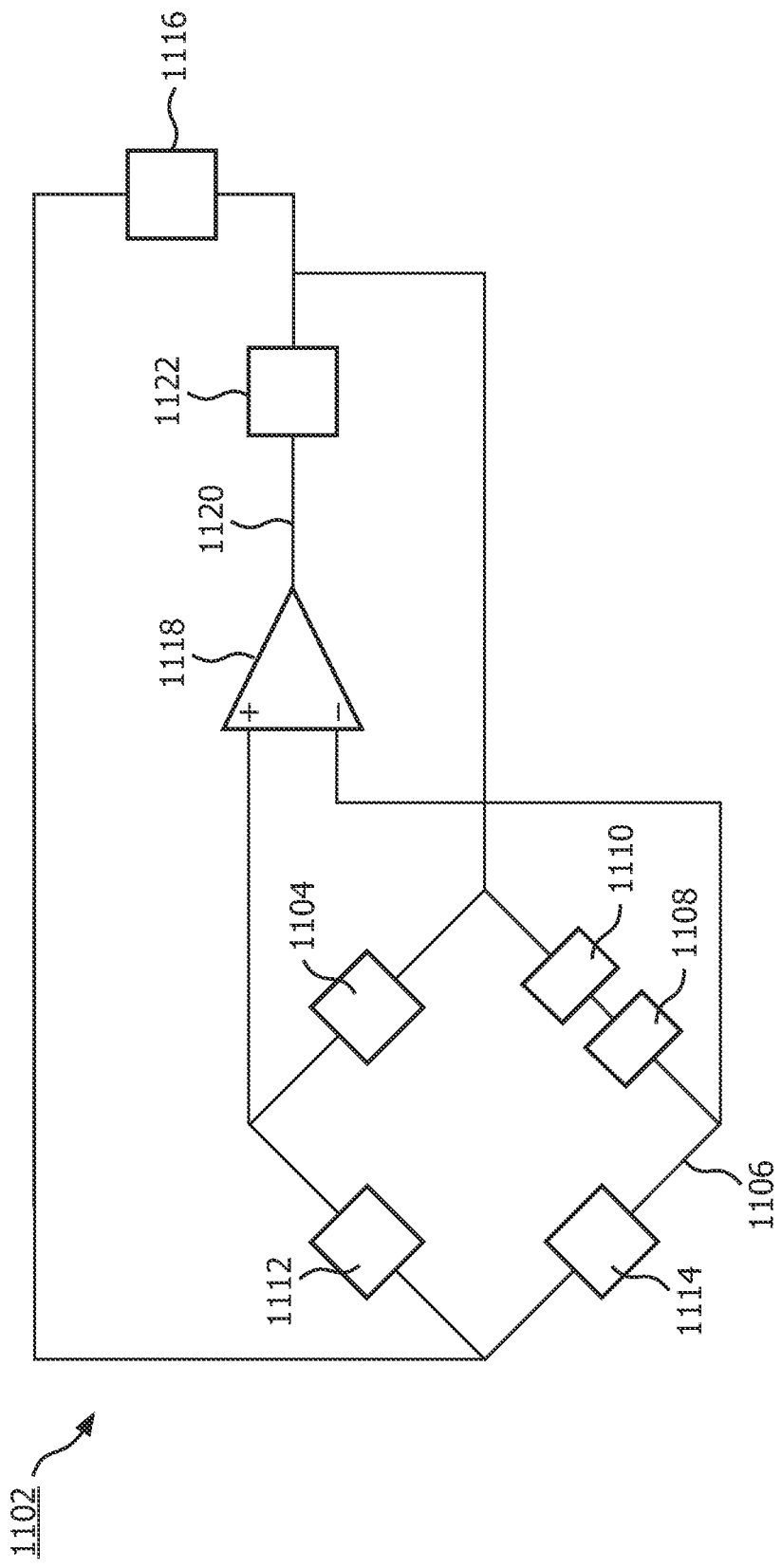
FIG. 11 schematically depicts an embodiment of an electronic circuit for materializing the sensor arrangement, the heating element and the control circuit according to the embodiment depicted in FIG. 4.

FIG. 11 schematically depicts an electronic circuit 1102 for materializing the temperature sensor 410, the heating embodiment 406 and the controller 418 according to the embodiment depicted in FIG. 4. The electronic circuit 1102 comprises a thermistor 1104 having a predetermined relation between its electrical resistance and its temperature performs as a heating element. Referring to FIG. 4, the thermistor is configured for heating the tube's distal end 408. Referring to FIG. 11, the thermistor 1104 is embedded in a Wheatstone bridge 1106. Fluctuations in ambient temperature are accounted for by situating a reference thermistor 1108 remotely from the thermistor 1104. Dissipation by the reference thermistor 1108 is prevented from by providing a resistor 1110 having a significantly large electrical resistance compared to the thermistor 1104. Additionally, the thermistor 1104 and the reference thermistor 1110 are provided with substantially equal temperature coefficients. Furthermore, resistors 1112 and 1114 are comprised in the Wheatstone bridge 1106. The resistors 1112 and 1114 are preferably provided with negligible temperature coefficients compared to the thermistor 1104. A voltage source 1116 applies a voltage across the Wheatstone bridge 1106. The electronic circuit 1102 comprises an operational amplifier (op-amp) 1118 for generating an output 1120 representative for a voltage difference across a leg of the Wheatstone bridge, which output 1120 is supplied to a controller 1122. In that way, a power provided to the thermistor 1104 is controlled. As a result, based on the predetermined relation between electrical resistance and temperature for the thermistor 1104, the thermistor's temperature is effectively maintained at a constant value.

While the invention has been illustrated and described in detail in the drawings and in the foregoing description, the illustrations and the description are to be considered illustrative or exemplary and not restrictive. It is noted that the apparatus and the system according to the invention and all their components can be made by applying processes and materials known per se. In the set of claims and the description the word "comprising" does not exclude other elements and the indefinite article "a" or "an" does not exclude a plurality. Any reference signs in the claims should not be construed as limiting the scope. It is further noted that all possible combinations of features defined in the set of claims are part of the invention.

The invention claimed is:

1. A system for exchanging a fluid, comprising:
  a tube having an opening at a distal end of the tube for flow of the fluid though the tube for introducing into or removing from a blood vessel the fluid, the tube including an apparatus for monitoring a position of the distal end of the tube with respect to the blood vessel to ascertain whether or not the distal end is located inside the blood vessel, the apparatus comprising:
  a heating element configured to heat the distal end,
  a sensor arrangement configured to generate a measurement signal indicative of heat transferred by an exterior of the distal end, wherein the measurement signal is equal to a reference level when a flow velocity in the blood vessel is minimum, and
  a comparator arrangement configured to compare the measurement signal with the reference level.

2. The system according to claim 1, wherein the sensor arrangement comprises a primary temperature sensor for measuring a temperature of the heating element while the heating element is provided with a constant level of power.

3. The system according to claim 2, wherein the sensor arrangement further comprises a secondary temperature sensor located at a remote location remote from the heating element not contacting the heating element for measuring a temperature at the remote location, and wherein the sensor arrangement is configured to measure a difference between temperatures measured by the primary and secondary temperature sensors.

4. The system according to claim 2, wherein the heating element comprises a thermistor having a predetermined relation between a resistance of the thermistor and a temperature of the thermistor, wherein the thermistor is embedded in a Wheatstone bridge, and wherein the primary temperature sensor comprises a Voltmeter for determining the resistance of the thermistor.

5. The system according to claim 1, further comprising a control circuit configured to control power provided to the heating element based on a deviation between a constant reference temperature and a temperature of the heating element measured by a primary temperature sensor, wherein the sensor arrangement is further configured to measure the power provided to the heating element.

6. The system according to claim 5, wherein the heating element comprises a thermistor having a predetermined relation between a resistance and a temperature of the thermistor, wherein the thermistor is embedded in a Wheatstone bridge, and wherein a voltage across a leg of the Wheatstone bridge comprising the thermistor is controlled by a feedback circuit during operation.

7. The system according to claim 1, wherein the sensor arrangement comprises a primary temperature sensor configured to measure a difference between temperatures at predetermined locations on both sides of the heating element along an axis having a component parallel to a longitudinal axis of the tube while the heating element is provided with a constant level of power during operation.

8. The system according to claim 1, wherein the sensor arrangement comprises a primary temperature sensor configured to measure a difference between temperatures at predetermined locations on both sides of the heating element along an axis having a component parallel to a longitudinal axis of the tube while power provided to the heating element during operation is controlled by a control circuit based on a deviation between a constant reference temperature and a temperature of the heating element measured by a secondary temperature sensor.

9. The system according to claim 1, wherein the sensor arrangement comprises a primary temperature sensor configured to measure a temperature of the distal end while the heating element is provided with power pulses during operation, wherein the sensor arrangement is configured to measure a duration after which heat pulses are detected by the primary temperature sensor.

10. The system according to claim 1, wherein the sensor arrangement comprises a primary temperature sensor and a secondary temperature sensor, wherein the primary and secondary temperature sensors are situated at locations on both sides of the heating element along an axis having a component parallel to a longitudinal axis of the tube, wherein the heating element is provided with power pulses during operation, and wherein the sensor arrangement is configured to measure a difference between durations after which heat pulses are detected by the primary and secondary temperature sensors.

11. The system according to claim 1, comprising an antenna for RF communication and a coil for receiving electromagnetic radiation for powering the heating element.

12. The system according to claim 1, wherein the heating element and the sensor arrangement are processed on a silicon substrate attached to a mechanically flexible carrier.

13. The system according to claim 12, wherein the sensor arrangement comprises a temperature sensor comprising a thermopile.

14. The system according to claim 1, wherein the heating element and the sensor arrangement are situated in a wall of the tube.

15. The system according to claim 1, wherein the heating element and the sensor arrangement are arranged substantially co-axially with the tube.

16. A method for exchanging a fluid, comprising acts of:
  providing a tube having an opening at a distal end of the tube for flow of the fluid though the tube for exchanging the fluid between the tube and a blood vessel;
  monitoring a position of the distal end of the tube with respect to the blood vessel to ascertain whether or not the distal end is located inside the blood vessel; and
  exchanging the fluid when the distal end is located inside the blood vessel, wherein the monitoring act further includes acts of:

heating the distal end by a heating element of the tube;

generating by a sensor arrangement of the tube a measurement signal indicative of heat transferred by an exterior of the distal end, wherein the measurement signal is equal to a reference level when a flow velocity in the blood vessel is minimum; and comparing the measurement signal with the reference level.

17. The method of claim 16, wherein the sensor arrangement comprises a primary temperature sensor for measuring a temperature of the heating element while the heating element is provided with a constant level of power.

18. The method of claim 17, wherein the sensor arrangement further comprises a secondary temperature sensor for measuring a temperature at a location remote from the heating element, and wherein the sensor arrangement is configured to measure a difference between temperatures measured by the primary and secondary temperature sensors.

19. The method of claim 17, wherein the heating element comprises a thermistor having a predetermined relation between a resistance of the thermistor and a temperature of the thermistor, wherein the thermistor is embedded in a Wheatstone bridge, and wherein the primary temperature sensor comprises a Voltmeter for determining the resistance of the thermistor.

* * * * *